(12) United States Patent
Wu et al.

(10) Patent No.: US 11,413,618 B2
(45) Date of Patent: Aug. 16, 2022

(54) DETECTION DEVICE

(71) Applicant: Hangzhou Biotest Biotech Co., LTD, Zhejiang (CN)

(72) Inventors: Shujiang Wu, Zhejiang (CN); Liang Hong, Zhejiang (CN); Jiang Liu, Zhejiang (CN); John Wu, Zhejiang (CN); Yangyu Zhu, San Diego, CA (US); Junsheng Wu, Zhejiang (CN)

(73) Assignee: HANGZHOU BIOTEST BIOTECH CO., LTD., Hangzhou (CN)

( * ) Notice: Subject to any disclaimer, the term of this patent is extended or adjusted under 35 U.S.C. 154(b) by 120 days.

(21) Appl. No.: 16/942,212

(22) Filed: Jul. 29, 2020

(65) Prior Publication Data

US 2021/0031203 A1 Feb. 4, 2021

Related U.S. Application Data

(60) Provisional application No. 62/882,709, filed on Aug. 5, 2019.

(30) Foreign Application Priority Data

Aug. 1, 2019 (CN) ........................ 201910708522.X

(51) Int. Cl.
*B01L 3/00* (2006.01)
*G01N 33/50* (2006.01)
(Continued)

(52) U.S. Cl.
CPC ...... *B01L 3/502792* (2013.01); *G01N 33/493* (2013.01); *G01N 33/50* (2013.01);
(Continued)

(58) Field of Classification Search
CPC ....... B01L 3/502792; B01L 2300/0663; B01L 2300/0816; B01L 2300/0819; B01L 2300/0825; B01L 2300/089; B01L 2300/161; B01L 2300/168; B01L 2400/0409; B01L 9/52; G01N 2033/0096; G01N 33/493; G01N 33/50; G01N 33/521; G01N 33/54386; G01N 33/558;
(Continued)

(56) References Cited

U.S. PATENT DOCUMENTS

| 7,008,799 B1* | 3/2006 | Zimmer | ................ B01L 3/5023 436/514 |
| 2019/0083490 A1* | 3/2019 | Saito | ...................... A61K 47/32 |

OTHER PUBLICATIONS https://www.early-pregnancy-tests.com/inpregtesstr, available Apr. 9, 2018, accessed Jan. 21, 2022. (Year: 2018).*

* cited by examiner

*Primary Examiner* — Jennifer Wecker
*Assistant Examiner* — Kathryn Elizabeth Limbaugh
(74) *Attorney, Agent, or Firm* — NZ Carr Law Office LLP

(57) ABSTRACT

The present invention provides a detection device, and the device comprises a testing element, wherein the testing element comprises a detection area used for detecting a presence of an analyte in a liquid sample; and a transparent area through which the test result on the detection area is read, and the transparent area includes a hydrophilic area and a hydrophobic area. Thus, the detection device reduces formation of droplets on the transparent area is reduced, that is, it avoids formation of a mist layer on the transparent area; or avoids accumulation of small droplets on the transparent area, thus to make the result on the test area be clearly read.

20 Claims, 3 Drawing Sheets

(51) Int. Cl.
*G01N 33/493* (2006.01)
*G01N 33/00* (2006.01)

(52) U.S. Cl.
CPC . *B01L 2300/089* (2013.01); *B01L 2300/0816* (2013.01); *B01L 2300/0819* (2013.01); *B01L 2400/0409* (2013.01); *G01N 2033/0096* (2013.01)

(58) Field of Classification Search
CPC ..... A61K 31/397; A61K 31/497; A61P 27/02; C07D 409/10; C07D 487/10; C07D 491/107
See application file for complete search history.

DETECTION DEVICE

CROSS REFERENCE OF THE RELATED APPLICATION

The present application claims the benefit of Chinese Patent Application No. 201910708522X, filed on Aug. 1, 2019, and U.S. patent Application No. 62/882,709, filed on Aug. 5, 2019. The content of these applications including all tables, diagrams and claims is incorporated hereby as reference in its entirety.

TECHNICAL FIELD

The present invention relates to a collection and detection device, in particular to a device for collecting and detecting a presence of an analyte in a liquid sample in the field of rapid diagnosis.

BACKGROUND

The following background art information is only a general introduction of the background and will not constitute any restrictions on the present invention.

A medical or household rapid detection device is generally used to detect a presence of an analyte in a sample, for example, for pregnancy test, drug detection, etc. The detection device is generally provided with a collecting chamber for collecting a sample to be tested (some do not have a liquid sample collecting chamber), and a testing element is installed in the collecting chamber. The sample to be tested enters into the collecting chamber through an opening of the collecting chamber and contacts the testing element, so that the testing element detects the sample to be tested. The testing element has a detection area for displaying a test result, and the test result can be read from outside the collecting chamber through the side wall of the collecting chamber. Generally, a part of the collecting chamber is transparent, and the result on the detection area is read through the transparent part. In some cases, the testing element does not read the test result immediately after detecting the sample collected in the collecting chamber, but sends it to the testing agency in batches for scanning and reading by a mechanical electronic device. Therefore, the detection device also comprises a cover body which fits with the collecting chamber to form a sealed chamber, and the sample and the testing element are sealed in the collecting chamber, thereby preventing the sample from being contaminated by the outside or the sample from being spilled or leaking from the collecting chamber during the transportation and transfer process.

Additionally, the testing element is generally located in a casing, within an area where the detection area of the testing element corresponds to the casing (the area of the casing is generally made of a transparent plastic or thin film), the detection area of the testing element is read through the transparent area of the casing, especially the color of the test line is used to judge whether the test result is positive or negative.

After detecting a sample, due to influence of certain factors, the existing collection and detection device may not be able to accurately read the test result on the testing element from outside the collecting chamber or the corresponding casing of the detection area. Hence, it is required to design and improve the traditional detection device to increase the convenience in using the detection device and the accuracy when reading the test result.

DETAILED DESCRIPTIONS OF THE INVENTION

To solve the above problems, one aspect of the present invention provides a collection and detection device, and the device has the advantages that it has simple structure and is convenient to manufacture, and can read the test result on the testing element from outside the collecting chamber clearly, quickly and conveniently without being affected by the external environment or the internal environment of the device.

In one aspect, the present invention provides a detection device, and the device comprises a testing element, wherein the testing element comprises a detection area used for detecting a presence of an analyte in a liquid sample; and a transparent area through which the test result on the detection area is read, and the transparent area includes a hydrophilic area and a hydrophobic area. Thus, the detection device reduces formation of droplets on the transparent area is reduced, that is, it avoids formation of a mist layer on the transparent area; or avoids accumulation of small droplets on the transparent area.

The hydrophilic area or the hydrophobic area herein is generally formed by overtreating the material that forms the transparent area or by selecting the transparent area directly formed by a hydrophilic or hydrophobic material. Selection or treatment of the material must be controlled to a certain degree to ensure no accumulation of small droplets may be or could be caused. The degree is adjusted freely depending on different products, storage temperatures, collected sample types or the external natural environment where the products are used. Changing to a hydrophilic area or a hydrophobic area can be understood as making the surface of the transparent area become more hydrophilic or hydrophobic than it is before surface treatment of the transparent area.

In some embodiments, the detection area has a side for displaying a test result, and the transparent area has a surface facing the surface for displaying a test result, and the surface facing the side for displaying a test result is coated with an anti-mist hydrophilic reagent or hydrophobic reagent.

In some embodiments, the transparent area does not necessarily include an anti-mist reagent, but after treatment by a physical method, the surface of the transparent area becomes hydrophilic and hydrophobic.

Regardless of the difference between the outside air temperature and the temperature of the transparent area, condensing of water droplets is reduced in the transparent area, or although water droplets are condensed they may quickly form a flat liquid layer, thereby not affecting reading of a test result on the testing element through the transparent area.

In some embodiments, the test area of the testing element displays the test result through a color change or a presence or absence of a color, that is, the test result is judge by reading a color change in the test area through the transparent area, and the reading may be achieved by naked eyes, a scanner, camera equipment, etc.

In some embodiments, the side of the transparent area that directly faces the test area has a layer of anti-mist reagent.

In some embodiments, the anti-mist reagent includes a hydrophilic reagent or a hydrophobic reagent. In some embodiments, the hydrophilic reagent contains a hydrophilic group. In some embodiments, the hydrophilic group absorbs water molecules in the air. In some embodiments, the anti-mist reagent contains a surfactant. In some embodiments, the surfactant contains one or several of xylitol ester, sorbitol monopalmitate, lauric acid or stearic acid monoglyceride.

In some embodiments, the detection area substantially and directly contacts the transparent area.

In some embodiments, the detection device comprises a carrier, and the testing element is arranged on the carrier.

In some embodiments, the carrier may be a part of a detection chamber, a part of a test card, or a part of a liquid sample collecting chamber.

In some embodiments, the transparent area is formed by a transparent material.

In some embodiments, the test area comprises a detection area and a control area of a test result.

In some embodiments, the material that forms the test area is different from the material that forms the transparent area.

In some embodiments, wherein the material of the test area is a porous absorbent material, and the material of the transparent area is a non-porous absorbent material.

In some embodiments, the material of the test area is nitrocellulose membrane or cellulose acetate membrane or nylon membrane; and the material of the transparent area is transparent glass, plastics, ceramics, plastic thin films, transparent double-sided adhesives, single-sided adhesives, transparent metal films or metal sheets.

In some embodiments, the transparent area is a part of the carrier, or the transparent area is made of the same material as the carrier, or the transparent area is arranged on the carrier.

In the other aspect, the present invention provides an application of an anti-mist reagent in preparation of a detection device having a testing element, the detection device comprises a carrier element, wherein the testing element is arranged on or in the carrier, wherein the device further comprises a transparent area, and the test result on the testing element is read through the transparent area.

Beneficiary Effects of the Present Invention:

The area of the testing element is coated with an anti-mist reagent, which can prevent the formation of water drops, thus to generate mist and make the test result on the test area is more clearly indicated through the transparent area.

DETAILED DESCRIPTION

Figure 1:
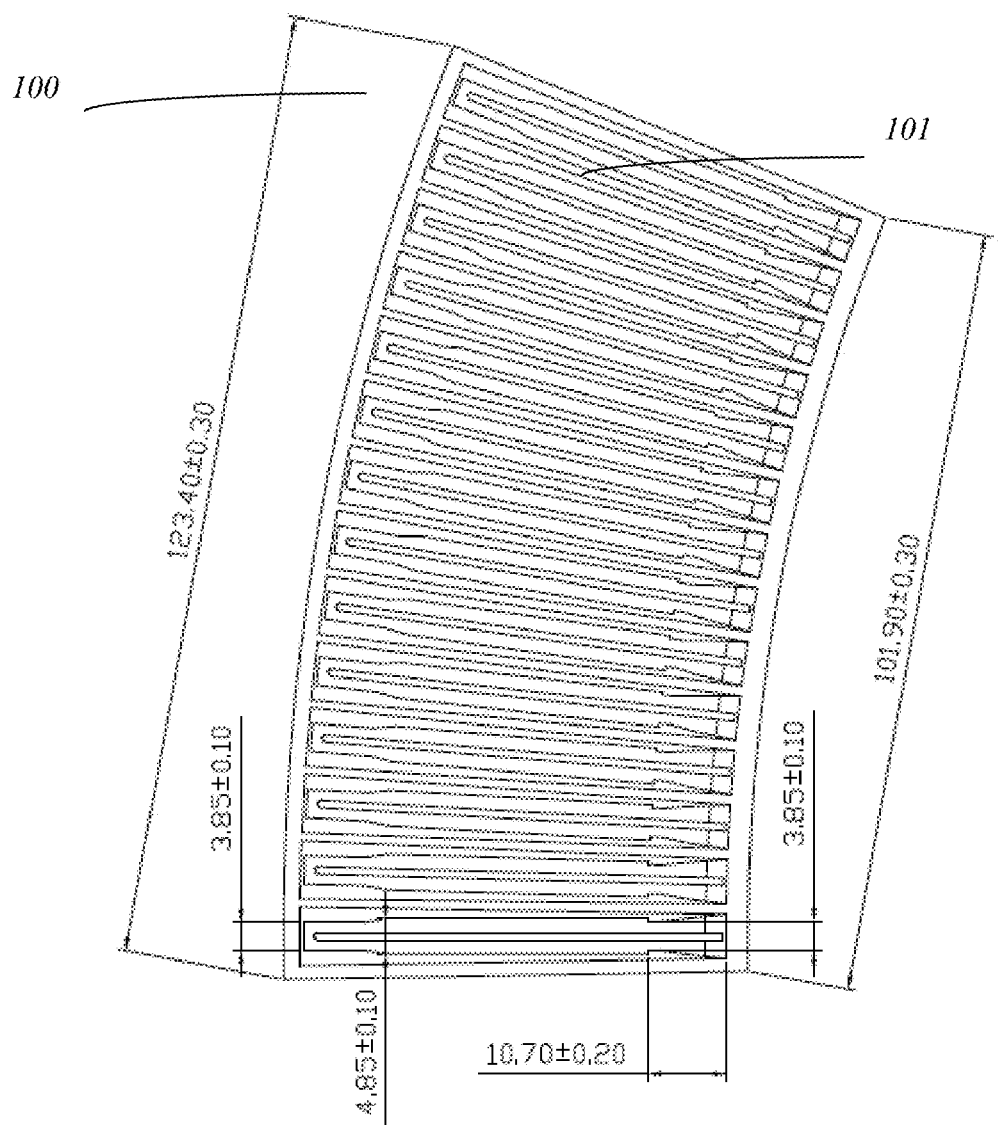
FIG. 1 depicts a stereogram of a test card according to an embodiment of the present invention

The following is a further explanation of the structures or of the technical terms involved in the invention, unless specifically specified, they will be understood and interpreted in accordance with the general terms in use in the field.

Detection

Detection means to conduct an experiment or a test to determine a presence of a substance or material. The substance or material, for example, but not limited to chemicals, organic compounds, inorganic compounds, metabolic products, drugs or drug metabolites, organic tissue or metabolites of organic tissues, nucleic acids, proteins, or polymers. In addition, detection can also indicate the quantity of a substance or material tested. Furthermore, a test also means immunity test, chemical test, enzyme test, etc.

Specimen

In the present invention, the specimen collected by the detection device includes a biological fluid. The specimen can be initially liquid, solid or semi-solid. A solid or semi-solid specimen can be converted into a liquid specimen by any suitable method of mixing, crashing, macerating, incubating, dissolving and enzymatic hydrolysis, and then pour into a collecting chamber and be tested for presence of an analyte. The specimen can be taken from a human body, an animal, a plant and nature. The specimen taken from the human body, can be a liquid specimen such as blood, serum, urine, cerebrospinal fluid, sweat, lymph, saliva, gastric fluid; or a solid or semi-solid specimen such as feces, hair, keratin, tartar, nail. The specimen taken from a plant may be solid specimens such as roots, stems and leaves; and also liquid or semi-solid specimens such as tissue fluids and cell fluids prepared from roots, stems and leaves. The specimen taken from the nature can be liquid specimens such as rainwater, river water, seawater, groundwater, etc.; and also solid or semi-solid specimens such as soil, rock, ore, petroleum, etc.

Fluid Exchange

In the present invention, the fluid refers to one or a mixture of gas, air, water vapor, or liquid. Fluid exchange means that a fluid flows from one area to another. Fluid exchange may be a passive exchange of a fluid under the action of an external force or an active exchange for the characteristics of a fluid itself. After a fluid exchange is blocked, the fluid in one area cannot flow to another area. A fluid exchange being blocked does not necessarily mean a presence of a liquid or gas, but, only in some cases, indicates a connection relationship or a state between the two areas; if there is a liquid or a gas in the area, one area is not in fluid communication with the other area.

Testing Element

The testing element refers to a component that can detect an analyte in a sample. The testing element can test an analyte based on any technical principles, for example, immunology, chemistry, electricity, optics, molecular science, physics, etc. The testing element of the present invention may be one kind or a combination of two or more kinds of testing elements. The testing element has a detection area for displaying a detection result, and the detection area displays the detection result after the detection.

A common form of the testing element is a test strip or a lateral flow strip. The test strip may test a test sample based on the principle of immunoassay or chemical analysis, and a non-competitive or competitive analysis mode may be applied. The test strip includes a sample feeding area, a reagent area and a detection area in order. After the test sample is added to the sample feeding area, it flows to the reagent area under a capillary action, reacts with the reagent in the reagent area and then flows further into the detection area under the capillary action, the detection area generates or does not generate a signal, to indicate a presence of an analyte in the test sample. For example, if a T line (Test Line) appears in the detection area, it indicates that there is no analyte in the test sample; if a T line does not appear in the detection area, it indicates that an analyte exists in the test sample. Some test strips also have a control area which is located behind the detection area, a sample flowing through the detection area continues to flow into the control area, and the control area is used for determining whether a test result in the detection area is valid. For example, in some test strips, the test result in the detection area is judged as valid only when a C line (Control Line) appears in the control area, otherwise, the test result in the detection area is invalid. In the present invention, when a test result of the testing element can be read only through the detection area, the detection area of the testing element is the aforesaid detection area; when the test result of the testing element must be judged by a signal generated by a detection area and a control area, the detection area of the testing element includes the detection area and the control area. Of course, in some cases, the test result of the testing element needs to be judged by a signal from other areas, then the detection area also includes the other areas. That is, in the present invention, a complete test result can be read through the detection area of the testing element. Generally, the testing element comprises at least a detection area, through which a presence or absence of an analyte in the sample can be determined. For example, through appearance or change of a color, the general color change is visible through naked eyes, the test result may read through scanning by a scanner, or by taking a picture. Or a fluorescence appears, or a ray appears, etc. Read the test result of the detection area by using a machine or instrument.

The testing element is generally composed of porous absorbent materials, such as any water-absorbing material of filter paper, glass fiber, polyester film, nylon film, paper sheet, non-woven fabric, etc. Generally, the material forming the test area is of absorbent materials, such as water absorbent film, nitrocellulose film, nylon film, etc.

Analyte

Examples that can use the analyte in the present invention include some hapten substances which include drugs (such as drug of abuse). "Drug of abuse" (DOA) refers to use of drugs for non-medical purposes (usually paralyzing nerves). Abuse of these drugs can lead to physical and mental damage, causing dependence, addiction and/or death. Examples of DOA include cocaine; amphetamine (AMP) (such as black beauty, white amphetamine tablets, dexamphetamine, dextroamphetamine tablets and Beans); methamphetamine (MET) (crank, meth, crystal and speed); barbiturate (BAR) (such as Valium □, Roche Pharmaceuticals, Nutley and New Jersey); sedatives (i.e. sleeping aids); lysergic acid diethylamide (LSD); inhibitors (downers, goofballs, barbs, blue devils, yellow jackets and methaqualone); tricyclic antidepressants (TCA, i.e. imipramine, amitriptyline and doxepin); methylenedioxy-methamphetamine (MDMA); phencyclidine (PCP); tetrahydrocannabinol (THC, pot, dope, hash, weed, etc.); opiate (i.e. morphine (MOP) or opium, cocaine (COC), heroin and hydroxycodeinone); and antianxietics and sedative hypnotics, wherein antianxietics are a class of drugs mainly used for reducing anxiety, tension and fear, stabilizing mood and having hypnotic and sedative effects, including benzodiazepines (BZO), atypical BZ, fusion diazepines NB23C, benzodiazepines, BZ receptor ligands, ring opening BZ, diphenylmethane derivatives, piperazine carboxylates, piperidine carboxylates, quinazolinones, thiazines and thiazole derivatives, other heterocyclics, imidazole sedatives/paregorics (such as oxycodone (OXY) and methadone (MTD)), propylene glycol derivatives-carbamates, aliphatic compounds, anthracene derivatives, etc. The detection device of the present invention can also be used for detecting drugs that belong to medical use but are prone to overdose, such as tricyclic antidepressants (imipramine or the like) and acetaminophen. After being absorbed by the human body, these drugs will be decomposed into different small molecule substances which are present in body fluids such as blood, urine, saliva, sweat or a part of the body fluid.

For example, the analytes detected by the present invention includes but not limited to, creatinine, bilirubin, nitrite, protein (non-specific), hormone (e.g. human chorionic gonadotropin, progesterone hormone, follicle stimulating hormone, etc.), blood, white blood cell, sugar, heavy metals or toxins, bacterial substance (e.g. proteins or sugars against specific bacteria, such as *Escherichia coli* 0157: H7, staphylococci, *salmonella, clostridium, campylobacter, L. monocytogenes, vibrio*, or cactus) and substances related to physical characteristics in urine sample, such as pH and specific gravity. Any other clinical chemical analysis of a urine can be detected by combination of a lateral cross-flow detection method and the device of the invention.

Transparent Area

The transparent area of the present invention is covered on a test strip, and the test result on the testing element is read through the transparent area. In some embodiments, the position of the transparent area matches the detection area of the testing element, or the detection area is arranged directly in front of or below the transparent area. In some embodiments, the transparent area is a transparent area, for example, transparent plastic, transparent film, transparent PVC, transparent glass, transparent metal and transparent ceramics, so that the test result on the testing element is read through the transparent area. "Reading" herein means to obtain a test result on the testing element through a transparent area, for example, reading by naked eyes or a device, such as a video camera, a camera, a scanner and photographing equipment, to obtain the test result automatically, of course, it may also be a fluorescent reading device or an X-ray reading device. It falls into the scope of the present invention as long as the detection result of a testing element is obtained by an optical means.

The material of the transparent area herein is generally transparent, and the detection area on the test area is read through the transparent area, the transparent material is generally plastic, PVC, transparent film, etc. These transparent areas may be arranged on the casing of the detection device, such as a test panel, a test cup, a test card or a part of these casings, or a part of the side wall of a liquid sample collecting chamber.

The transparent area may present a multi-layer structure, for example a combination of multiple transparent layers, as long as an anti-mist reagent is coated on the surface of these multiple transparent areas, droplets may be reduced or mist phenomenon is avoided, so that the test area displays the result more clearly, thereby making it easier to read the result of the test area.

Therefore, at this time, if the transparent area has a "mist" phenomenon, for example, the attachment of small droplets or tiny droplets, the transparent area may not display clearly, and sometimes the test result on the testing element is covered, because the light is hard to penetrate through or it has refraction or reflection, or these tiny droplets cover the test area and the does not pass through easily, thus to cause unfavorable result of inaccurate reading or fail to obtain the test result. The water droplets of the film are attached to the transparent area, which makes the test area blurry, thereby resulting in inaccuracy of the result.

"Misting" is generally a process when there is a temperature difference between two media, for example, there is a temperature difference between the transparent area and the air, for example, the temperature of the transparent area is low, while the temperature of the air is high; and the air generally contains water vapors, when encountering low temperature, water vapors will condense into small droplets. The quantity and speed of droplets produced are directly related to the difference in temperature and the humidity of the air. In a micro environment, if the air humidity is high and the temperature difference is large, the speed of generating small droplets would be fast, and the density on the transparent area would be high; on the contrary, if one of the conditions of the air humidity or temperature difference changes, the quantity and speed of small droplets could be impacted. To reduce the occurrence of mist between the detection area and the transparent area, on one hand, the air humidity should be reduced or the difference between the transparent area and the ambient temperature should be reduced. When using the test device, it is generally hard to quickly change the temperature difference between the transparent area of the detection device and the environment, while the humidity of the air contacting the transparent area can be easily changed, for example, by reducing the amount of humid air from entering into the space between the detection area and the transparent area. Increasing the humidity of the air between the two slowly can reduce the humidity of the air between the two, for example, the humidity of the air between the two increases to the condition where mist occurs in 1 minute, 2 minutes, 10 minutes, 20 minutes, 30 minutes, 50 minutes, 1 hour and 2 hours (with the difference between the transparent area and the ambient temperature unchanged), and when there is a very small gap between the detection area and the transparent area. Or, the humid air is prevented from entering into or actually entering the space between the detection area and the transparent area, for example, a relatively sealed space formed by the detection area and the transparent area. In another embodiment, the detection area contacts with the transparent area or the two have a small gap so that the generated small droplets contacts the detection area, and then absorbed by the detection area composed of porous absorbent materials while forming a liquid, in this way, mist phenomenon in the transparent area is reduced, and the test result is read more clearly.

This is because, in the existing traditional products, the detection area is arranged in an environment wrapped by an outer casing (made of plastic, or PCV material), such as, a pregnancy test device, or on some carriers, or in a test board; for example in the device described in the United States (U.S. Pat. No. 9,414,813, but the detection area of the testing element may have a gas or liquid exchange with the outside. Generally, the area corresponding to the detection area is generally transparent, through which the test result on the detection area can be read (by naked eyes, a scanner, a camera or other equipment) through a transparent part. Generally, the device is pre-stored at a low temperature, and is taken out and incubated for a period of time at the room temperature when a test is required; at this time, as the temperature of the entire detection device is low while the outdoor temperature is high, the water vapor in the outside air will condense into the form of tiny water droplets or mist on the surface of the test device, these tiny water droplets or mist can be wiped off if on the outer surface of the casing, but if they enter into a place between the detection area and the transparent area or enter into an internal space around the detection area, small droplets or mists may form on the transparent inner surface, thus to cover the indication of the test result in the detection area.

In another situation, when the temperature of the external environment is relatively low (such as in winter), and the temperature of the liquid sample is sometimes higher than the temperature of the external environment, for example, the temperature of the urine is 35-37° C., this time, at a low temperature, the temperature of the test device or the temperature of the external casing is generally lower than the temperature of the sample, so there is a temperature difference, at this time, because a gas or liquid exchange with the outside would occur around the detection area, the liquid and the micro atmospheric environment have a moisture exchange, and the humidity in the micro environment increases, then the liquid may also flow into the space around the detection area, or may form tiny water droplets around the detection area or the detection area, thus to form a layer of tiny water droplets on the transparent casing. Sometimes, it may be a combination of the above two factors, in short, the detection device has a temperature difference with the outside and/or the detection device has a temperature difference with the liquid sample, generally when the temperature of the detection device is lower than the outside temperature or/and lower than the temperature of the liquid sample, tiny water droplets will form on the walls around the detection area, this is a process of mist, which forms a pattern like a frosted glass; after detection, a layer of tiny water droplets or something like mists may condense or form on the transparent part, this may affect the accuracy of reading the test result on the detection area. Especially when the detection area is located between positive area or negative area, mist almost covers the result of the detection area, so that the result may not be read or the result may not be read accurately. Sometimes, even if a result is indicated in the detection area, due to the effect of mist, when using a scanner, the result that is consistent with the actual situation cannot be obtained or the test result obtained is wrong.

In some embodiments, the testing element is generally combined with a sample collector or a chamber, for example, the detection device comprises a collecting chamber, and a testing element is installed in the collecting chamber, the testing element has a detection area which is near a side wall of the collecting chamber relative to the back of the detection area, and through the side wall of the collecting chamber the test result displayed in the detection area of the testing element can be read from outside the collecting chamber. However, in the existing detection device, after the testing element is installed in the collecting chamber, there is a gap between the testing element and the inner wall of the collecting chamber, especially a gap between the detection area of the testing element and the inner wall of the collecting chamber, and the gap is in fluid communication with the surroundings (such as other areas or spaces in the collecting chamber), or the gap and the surroundings are in fluid communication state. After the surrounding fluid (such as liquid or air) enters into the gap, mist phenomenon may form in the detection area of the testing element, thereby blocking the detection area of the testing element, at this time, the test result in the detection area cannot be accurately read from outside the collecting chamber, and the use of the detection device may be affected.

The most common example is that when the temperature of the test sample in the collecting chamber is higher than that of the inner wall of the collecting chamber or the environment (for example, when testing a warm body fluid just collected in winter or at a low room temperature), the moisture in the sample evaporates into gas (water vapor), enters into the gap between the detection area of the testing element and the inner wall of the collecting chamber and condenses into water droplets or tiny water droplets or fluid droplets on the inner wall of the collecting chamber. The refraction effect of water droplets on light may cause a deviation between the read test result and the actual test result. For example, because there is a short distance between the detection area and the control area of the test strip, under the refraction effect of water droplets, it may be difficult to judge whether a T line or a C line is indicated. If the water droplets formed are very tiny, the tiny water droplets change the originally smooth and transparent inner wall of the collecting chamber into a form like a "frosted glass", in this case, it is impossible to read the test result cannot from outside the collecting chamber. Another example is that the sample collected in the collecting chamber evaporates into colored gas, and then enters into the gap between the detection area and the inner wall of the collecting chamber, thus to cover the test result. Another example is that when a liquid sample sputters in the collecting chamber, enters into a gap between the detection area of the testing element and the inner wall of the collecting chamber in the form of small droplets and attaches onto the inner wall of the collecting chamber, the test result would be covered, especially when the liquid sample itself is turbid or non-transparent, such as blood, turbid urine, and tissue fluid, the blocking effect may be more obvious.

The present invention designs a collection and detection device which comprises a transparent area and a testing element having a detection area, when the testing element is combined with the transparent area, the transparent area can reduce or block the area between the detection area and the transparent area, and have fluid exchange with the surrounding. In the existing detection device, there is a large gap between the detection area and the inner wall of the collecting chamber, and the detection device is not provided with any component for reducing the size and dimension of the gap, and the gap is in full fluid communication with the surrounding, so that the fluid around the gap can enter into the gap, enables mist, condensation or blocks the test result due to the characteristics of the fluid itself.

The present invention reduces the fluid exchange between the area between the detection area and the transparent area and the surrounding, so that the amount of surrounding fluid entering into the area is reduced, thereby weakening the blocking effect of the fluid on the test result. The reduction of the fluid exchange of the area between the detection area and the transparent area with the surrounding can be any value relative to the existing detection device, for example 5%, 25%, 50%, 80%, 90% . . . , blocking the fluid exchange of the area between the detection area and the inner wall of the transparent area with the surrounding makes no more liquid exchange and gas exchange of the area between the detection area and the inner wall of the transparent area with the surrounding, or no liquid exchange or gas exchange at all. When there is no liquid exchange between the area between the detection area and the inner wall of the transparent area, and the surrounding, after collecting a sample in the collecting chamber, the liquid substance originating from the sample cannot enter into the area between the detection area and the inner wall of the collecting chamber. The liquid substance may be the sample itself, water formed by evaporation and condensation of moisture in the sample, the water solution containing some dissolved substance in the sample, or a substance generated by the sample in other forms. When there is no gas exchange between the area between the detection area and the inner wall of the transparent area, and the surrounding, after collecting a sample in the collecting chamber, the gaseous substance originating from the sample cannot enter into the area between the detection area and the inner wall of the collecting chamber. The gaseous substance may be a substance formed by volatilization, evaporation, reaction of the sample or other forms. When there is no liquid exchange or gas exchange between the area between the detection area and the inner wall of the transparent area, and the surrounding, after collecting a sample in the collecting chamber, the liquid substance and gaseous substance originating from the sample cannot enter into the area between the detection area and the inner wall of the collecting chamber. In some preferred embodiments, a fluid is a gas and/or liquid. In some preferred embodiments, when the testing element is combined with the transparent area, the area between the detection area and the inner wall of the transparent area is gas-sealed. In some preferred embodiments, when the testing element is combined with the transparent area, the area between the detection area and the inner wall of the collecting chamber is liquid-sealed. When no liquid substance enters, if a temperature difference exists, mist is avoided and the result on the detection area can be read correctly.

There are two embodiments to reduce or block the fluid exchange of the area between the detection area and the inner wall of the transparent area, with the surrounding: in the first embodiment, the inner wall of the transparent area attaches to the detection area. For example, the transparent area is a part of a cup collecting chamber, such as a part of the wall of the cup body, a pressure is applied to the back of the testing element to press the detection area of the testing element against the inner wall of the collecting chamber, thereby reducing the size and dimension of the gap between the detection area and the inner wall of the collecting chamber, and even eliminating the gap between the detection area and the inner wall of the collecting chamber. In the second embodiment, the area between the detection area and the inner wall of the transparent area is filled up. That is, the dimension and size of the area between the detection area and the inner wall of the transparent area is reduced by filling the gap. In some preferred embodiments, the area between the detection area and the inner wall of the transparent area can be filled. In some preferred embodiments, the inner wall of the transparent area is made of a transparent or semi-transparent material. In this way, from the outside of the collecting chamber, the test result indicated on the detection area can be read through the transparent area. The blocking element in two embodiments are described in detail below.

This is because, in the existing traditional products, the detection area is arranged in an environment wrapped by an outer casing (made of plastic, or PCV material), such as, a pregnancy test device, or on some carriers, or in a test board; for example in the device described in the United States (U.S. Pat. No. 9,414,813, but the detection area of the testing element may have a gas or liquid exchange with the outside. Generally, the area corresponding to the detection area is generally transparent, through which the test result on the detection area can be read (by naked eyes, a scanner, a camera or other equipment) through a transparent part. Generally, the device is pre-stored at a low temperature, and is taken out and incubated for a period of time at the room temperature when a test is required; at this time, as the temperature of the entire detection device is low while the outdoor temperature is high, the water vapor in the outside air will condense into the form of tiny water droplets or mist on the surface of the test device, these tiny water droplets or mist can be wiped off if on the outer surface of the casing, but if they enter into a place between the detection area and the transparent area or enter into an internal space around the detection area, small droplets or mists may form on the transparent inner surface. In another situation, when the temperature of the external environment is relatively low (such as in winter), and the temperature of the liquid sample is sometimes higher than the temperature of the external environment, for example, the temperature of the urine is 35-37° C., this time, at a low temperature, the temperature of the test device or the temperature of the external casing is generally lower than the temperature of the sample, so there is a temperature difference, at this time, because a gas or liquid exchange with the outside would occur around the detection area, the liquid and the micro atmospheric environment have a moisture exchange, and the humidity in the micro environment increases, then the liquid may also flow into the space around the detection area, or may form tiny water droplets around the detection area or the detection area, thus to form a layer of tiny water droplets on the transparent casing. Sometimes, it may be a combination of the above two factors, in short, the detection device has a temperature difference with the outside and/or the detection device has a temperature difference with the liquid sample, generally when the temperature of the detection device is lower than the outside temperature or/and lower than the temperature of the liquid sample, tiny water droplets will form on the walls around the detection area, this is a process of mist, which forms a pattern like a frosted glass; after detection, a layer of tiny water droplets or something like mists may condense or form on the transparent part, this may affect the accuracy of reading the test result on the detection area. Especially when the detection area is located between positive area or negative area, mist almost covers the result of the detection area, so that the result may not be read or the result may not be read accurately. Sometimes, even if a result is indicated in the detection area, due to the effect of mist, when using a scanner, the result that is consistent with the actual situation cannot be obtained or the test result obtained is wrong.

In some embodiments, the testing element is generally combined with a sample collector or a chamber, for example, the detection device comprises a collecting chamber, and a testing element is installed in the collecting chamber, the testing element has a detection area which is near a side wall of the collecting chamber relative to the back of the detection area, and through the side wall of the collecting chamber the test result displayed in the detection area of the testing element can be read from outside the collecting chamber. However, in the existing detection device, after the testing element is installed in the collecting chamber, there is a gap between the testing element and the inner wall of the collecting chamber, especially a gap between the detection area of the testing element and the inner wall of the collecting chamber, and the gap is in fluid communication with the surroundings (such as other areas or spaces in the collecting chamber), or the gap and the surroundings are in fluid communication state. After the surrounding fluid (such as liquid or air) enters into the gap, mist phenomenon may form in the detection area of the testing element, thereby blocking the detection area of the testing element, at this time, the test result in the detection area cannot be accurately read from outside the collecting chamber, and the use of the detection device may be affected. The most common example is that when the temperature of the test sample in the collecting chamber is higher than that of the inner wall of the collecting chamber or the environment (for example, when testing a warm body fluid just collected in winter or at a low room temperature), the moisture in the sample evaporates into gas, enters into the gap between the detection area of the testing element and the inner wall of the collecting chamber and condenses into water droplets or tiny water droplets or fluid droplets on the inner wall of the collecting chamber. The refraction effect of water droplets on light may cause a deviation between the read test result and the actual test result. For example, because there is a short distance between the detection area and the control area of the test strip, under the refraction effect of water droplets, it may be difficult to judge whether a T line or a C line is indicated. If the water droplets formed are very tiny, the tiny water droplets change the originally smooth and transparent inner wall of the collecting chamber into a form like a "frosted glass", in this case, it is impossible to read the test result cannot from outside the collecting chamber. Another example is that the sample collected in the collecting chamber evaporates into colored gas, and then enters into the gap between the detection area and the inner wall of the collecting chamber, thus to cover the test result. Another example is that when a liquid sample sputters in the collecting chamber, enters into a gap between the detection area of the testing element and the inner wall of the collecting chamber in the form of small droplets and attaches onto the inner wall of the collecting chamber, the test result would be covered, especially when the liquid sample itself is turbid or non-transparent, such as blood, turbid urine, and tissue fluid, the blocking effect may be more obvious.

The present invention designs a collection and detection device which comprises a blocking element, when the testing element is combined with a collecting chamber, the blocking element reduces or blocks the fluid exchange between the area between the detection area and an inner wall of the collecting chamber and the surrounding. In the existing detection device, there is a gap between the detection area and the inner wall of the collecting chamber, and the detection device is not provided with any component for reducing the size and dimension of the gap, and the gap is in full fluid communication with the surrounding, so that the fluid around the gap can enter into the gap, enables mist, condensation or blocks the test result due to the characteristics of the fluid itself. The present invention reduces the fluid exchange between the area between the detection area and the inner wall of the collecting chamber and the surrounding through a blocking element, so that the amount of surrounding fluid entering into the area is reduced, thereby weakening the blocking effect of the fluid on the test result. The reduction of the fluid exchange of the area between the detection area and the inner wall of the collecting chamber with the surrounding can be any value relative to the existing detection device, for example 5%, 25%, 50%, 80%, 90% . . . , blocking the fluid exchange of the area between the detection area and the inner wall of the collecting chamber with the surrounding makes no more liquid exchange and gas exchange of the area between the detection area and the inner wall of the transparent area with the surrounding, or no liquid exchange or gas exchange at all. When there is no liquid exchange between the area between the detection area and the inner wall of the collecting chamber and the surrounding, after collecting a sample in the collecting chamber, the liquid substance originating from the sample cannot enter into the area between the detection area and the inner wall of the collecting chamber. The liquid substance may be the sample itself, water formed by evaporation and condensation of moisture in the sample, the water solution containing some dissolved substance in the sample, or a substance generated by the sample in other forms. When there is no gas exchange between the area between the detection area and the inner wall of the collecting chamber, and the surrounding, after collecting a sample in the collecting chamber, the gaseous substance originating from the sample cannot enter into the area between the detection area and the inner wall of the collecting chamber. The gaseous substance may be a substance formed by volatilization, evaporation, reaction of the sample or other forms. When there is no liquid exchange or gas exchange between the area between the detection area and the inner wall of the collecting chamber, and the surrounding, after collecting a sample in the collecting chamber, the liquid substance and gaseous substance originating from the sample cannot enter into the area between the detection area and the inner wall of the collecting chamber. In some preferred embodiments, a fluid is a gas and/or liquid. In some preferred embodiments, when the testing element is combined with the collecting chamber, the area between the detection area and the inner wall of the collecting chamber is gas-sealed. In some preferred embodiments, when the testing element is combined with the collecting chamber, the area between the detection area and the inner wall of the collecting chamber is liquid-sealed. When no liquid substance enters, if a temperature difference exists, mist is avoided and the result on the detection area can be read correctly.

In the present invention, the blocking element only reduces or blocks the fluid exchange between the area between the detection area and an inner wall of the collecting chamber and the surrounding during the detection process, for example, the detection process starts with collection of a sample in the collecting chamber and ends with reading a test result. Of course, the blocking element acts on its effect of reducing or blocking the fluid exchange before collecting a sample in the collecting chamber and continues the effect until a test result is read; or, from time of combination of the testing element and the collecting chamber, the blocking element continues to exert the effect of reducing or blocking the fluid exchange. As along as the blocking element reduces or blocks the fluid exchange between the area between the detection area and an inner wall of the collecting chamber and the surrounding, the interference of external factors on reading a test result is reduced or avoided.

There are two embodiments to reduce or block the fluid exchange between the area between the detection area and the inner wall of the collecting chamber and the surrounding: in the first embodiment, the blocking element makes the detection area attached to the inner wall of the collecting chamber. In other words, the blocking element applies a pressure to the back of the testing element and presses the detection area of the testing element against the inner wall of the collecting chamber, thereby reducing the size and dimension of the gap between the detection area and the inner wall of the collecting chamber, and even eliminating the gap between the detection area and the inner wall of the collecting chamber. In the second embodiment, the blocking element fills up the area between the detection area and the inner wall of the collecting chamber; That is, the dimension and size of the area between the detection area and the inner wall of the collecting chamber is reduced by filling the gap. In some preferred embodiments, the blocking element fills up the area between the detection area and the inner wall of the transparent area. In some preferred embodiments, the blocking element is made of a transparent or semi-transparent material. In this way, from the outside of the collecting chamber, the test result displayed on the detection area can be read through a second blocking element.

In some other embodiments, the surface of the transparent area is treated with some chemicals to reduce droplets' ability to attach to the surface of the transparent area, such as water drops, for example if the transparent area is hydrophobic or it is a hydrophobic smooth surface, the droplets could not or is difficult to attach to the surface. Or, even if it is attached in the form of droplets, it does not exist in the form of water droplets, but it is covered in a layered form, in this way the quantity of droplets may be reduced, for example on a hydrophilic surface, once there are water droplets formed, the surface becomes wet as it is a hydrophilic surface, the droplets may be moistened to a water layer covering the transparent surface, thus reducing the formation of droplets or quantity of droplets. Details are elaborated and explained below.

In some embodiments, the transparent area being arranged on a carrier, is a part of a carrier for carrying a testing element, for example, a carrier may be a test card, a test midstream, or a test cup. The transparent material is generally a transparent material, and optionally a transparent plastic material.

Hydrophobic Surface or Hydrophobic Reagent

The surface of the transparent area may be a hydrophobic surface, so that even if water droplets are formed, they are difficult to adhere to the surface, thereby reducing the adhesion ability of the droplets, reducing the droplets in the transparent area and mist phenomenon. There are many embodiments for changing a transparent surface to a hydrophobic one, for example, changing the surface into a hydrophobic one by using a hydrophobic compound, such as fatty and/or aromatic compounds, various inks and polymers. The compound is generally soluble in organic solvents or a mixture containing water and organic solvents. U.S. Pat. No. 7,824,611 (included in the references herein) discloses suitable technologies (i.e., ink-jet printing, spray painting, screen printing, sketching, embossing, etc.), and the technologies enable application of the hydrophobic area on the surface.

For example, U.S. Pat. No. 7,824,611 discloses a series of technologies, which are used for preparing hydrophobic surfaces. For hydrophilic surfaces, the hydrophobic area could be formed by using organic solvents, the application of these organic solvents disrupts the plasma treatment or denatures the protein to recreate the original hydrophobic plastic surface or create a hydrophobic surface by denaturing the protein, or uses a focused laser beam for local heating of the surface to destroy the hydrophilicity of the surface. Alternatively, any of the methods described above is used to create a hydrophobic area before creating any hydrophilic area. These areas can be covered up by some items, such as the template may be covered by some materials applied on the surface masked, which materials are then removed.

In one embodiment, the hydrophobic surface is created by starting from a hydrophobic surface, such as being found in natural plastics and elastomers (polyethylene, polypropylene, polystyrene, polyacrylate, silicone elastomer, etc.). In one embodiment, hydrophobic particles may be stored on the surface. Such particles contain latex particles, such as polypropylene latex or hydrophobic polymers (like polypropylene, polyethylene and polyester) with a diameter between about 0.01 microns and 10 microns. In another embodiment, the hydrophobic surface is created through application of hydrophobic compounds, such as inks or long-chain fatty acids, or application of a hydrophobic decal to the desired area. Hydrophobic compounds or decals are generally not soluble or insoluble in a reaction mixture. In another preferred embodiment, the hydrophobic surface may be formed by changing a hydrophilic surface to a hydrophobic surface. For example, a hydrophilic hydrophobic surface created by plasma treatment is converted to a hydrophobic surface through application of solvents, ultraviolet light, or heat. These treatments may be used to change a hydrophilic surface, to make a plasma-modified molecular structure back to the hydrophobic form.

As discussed above, the hydrophobic compounds in the present invention, for example, fatty and/or aromatic compounds and various inks and polymers, may be used to create a hydrophobic area. The compound is generally soluble in organic solvents or a mixture of water and organic solvents. Those skilled in the art will acknowledge that various techniques known in the field (i.e. ink-jet printing, spray coating, screen printing, painting, embossing, etc.) are those that allow application of a hydrophobic area on or in a surface.

Hydrophilicity

In some embodiments, the surface of the transparent area is hydrophilic, which has an attachment to water, when tiny water droplets are formed on the surface, the water may be easily moistened, so that the spherical water droplets diffuse into non-spherical droplets, thereby increasing the projection of light. Hydrophilicity means hydrophilic property or hydrophilicity, in specific, it means the molecules with polar groups have a great affinity for water, so that they may absorb water molecules, or easily soluble in water. The molecules with polar groups have a great affinity for water, so that they may absorb water molecules, or easily soluble in water. The surface of a solid material formed by such molecules is easily moistened by water. Having such a characteristic means having hydrophilic property.

Hydrophilicity refers to a physical property that molecules form short-lived bonds through hydrogen bonds and water. As it is proper in thermodynamics, this molecule may not only dissolve in water, but also in other polar solutions. A hydrophilic molecule, or a hydrophilic part of a molecule, means it is able to polarize to an area where hydrogen bonds are formed, and dissolve in water easier than in oil or other hydrophobic solutions.

The material is hydrophilous. Metal sheets, such as chromium, aluminum, zinc and the resulting hydroxides and substances with capillary phenomena, have good hydrophilic effects. Different components have different hydrophilicity, which can be selected as needed. The property of being easy to form a hydrogen bond with water is hydrophilicity. Many hydrophilic groups, such as hydroxyl, carboxyl, amino, sulfonic group, are easily bonded to hydrogen, so they are hydrophilic.

Hydrophilicity is a property of being wetted by moisture on a material surface It is an interface phenomenon, the wetting process is actually a change of the nature and energy of a material interface. When the cohesion between water molecules is less than the mutual attraction between water molecules and solid material molecules, the material is wetted by water, and then the material becomes hydrophilic, called a hydrophilic material; while the cohesion between water molecules is greater than the attraction between water molecules and material molecules, the surface of the material is not wetted by water, the material is hydrophobic, called a hydrophobic material.

The interactions between water molecules and the surface of different solid materials are different. At an intersection of the three phases of water (liquid phase), material (solid phase) and air (gas phase), an angle $\theta$ formed by a tangent line along the surface of water drops and the contact surface of water and the material is called a contact angle (as shown in FIG.), the angle $\theta$ is between 0° and 180°, and the wetting degrees may be estimated from the size of the angle $\theta$. Smaller angle $\theta$, indicates better wettability. If $\theta=0°$, the material is completely wetted; if $\theta<90°$ (such as glass, concrete and various mineral surfaces), the material is hydrophilic; $\theta>90°$ (for example, water droplets on the surface of paraffin and asphalt), the material is hydrophobic; when $\theta=180°$, the material is completely non-wet.

Anti-mist reagent is a special hydrophilic agent, a low-molecular-weight dispersant containing hydrophilic groups, it is composed of molecules with a determined molecular weight, and coated on a surface of a transparent object to a coating, the hydrophilic groups in the coating absorb water molecules in the air, the water molecules are then wetted on the surface of the transparent object and diffuse to form a water film (other than water droplets), so that the light penetrating through the object may not be scattered, thus to avoid mist phenomenon. An instant anti-mist reagent is mainly composed of a surfactant, such as xylitol ester, sorbitol monopalmitate, lauric acid or hard resin monoglyceride and the like; it has the disadvantages that the anti-mist duration is short, the adhesion is poor, generally in several days or a dozen of days the anti-mist effect disappears immediately after wiping or rinsing with water, therefore, it may not be used as a long-acting anti-mist reagent. But these are used in the present invention to show an inner surface or outer surface of a transparent area.

The working mechanism of an anti-mist reagent is application of a special molecular structure of polyalcohol nonionic surface activity, a part of which is a hydrophilic group, and a part thereof is a lipophilic group; wherein the hydrophilic group adsorbs water molecules in the air and reduces its surface tension to reduce a contact angle between the water molecules and the surface of the transparent object, so that the water molecules are wetted and diffuse on the surface of the transparent object before forming tiny water drops on the surface of the transparent object, thus to form a layer of ultra-thin transparent water film; no scattering effect is then made on the incident light and the vision is not interfere, thereby prevent mist generation. Common polyalcohol nonionic surfactants include glycerin esters, polyglycerin esters, sorbitan esters, ethoxylated derivatives, ethoxylated nonylphenol, ethoxylated alcohols, etc.

The main component of an anti-mist reagent is a surfactant, and the molecular structure of the surfactant is amphiphilic: one end is a hydrophilic group, and the other end is a hydrophobic group. The hydrophilic group absorbs water molecules to form a water film, showing a good anti-mist effect; the hydrophobic group causes the water film to have fluidity and drive the surfactant to scatter and disappear together, so that the anti-mist effect of the anti-mist reagent disappears accordingly, which will greatly shorten the anti-mist duration of the anti-mist reagent. In another aspect, the surfactant also has sensitivity to water (highly soluble in water), when a surface of the transparent object coated with an anti-mist reagent is flushed with water, the anti-mist reagent coating on the surface, i.e. surfactant, is quickly dissolved in the water and taken away by the flowing water, then its anti-mist function would be lost accordingly. Moreover, after the anti-mist agent is coated on the surface of a transparent object, it may not form a continuous film due to the interference of a hydrophobic group, but may be adsorbed on the surface of the object without strong adhesion, the anti-mist reagent is easily wiped off by a cloth, thus the anti-mist function is lost. Therefore, water washing and wiping are a nemesis of an anti-mist reagent. An anti-mist agent has sound anti-mist effect, but the anti-mist duration is short, no wiping and water washing are the biggest limitation of the anti-mist reagent. Despite these disadvantages, it could still be used in the present invention for preventing generation of water droplets.

An internal anti-mist reagent has a long-term effect, and it is widely used. When an internal anti-mist reagent is added to a polymer matrix, it may migrate onto the surface of a plastic film. After the anti-mist reagent on the surface is lost due to abrasion of a washing machine, the anti-mist reagent inside the polymer re-migrates onto the surface of the material for replenishment until the anti-mist reagent contained in the plastic material is fully exhausted. It has the characteristic of long-term efficiency, but the processing cost and the dosage of the anti-mist reagent are higher.

The material of the transparent area herein is generally transparent, and the detection area on the test area is read through the transparent area, the transparent material is generally plastic, PVC, transparent film, etc. Of course, these transparent areas may be located on a casing of the detection device, such as a panel, a cup, a test card, or a part of these casings.

The present invention designs a collection and detection device, a reagent is applied on the transparent area to make the surface hydrophilic or hydrophobic, so that small water droplets are not easily formed on the surface, the reduction this the case of not processing any reagents; compared with the situation where a reagent is not applied, the reduction value may be any value, such as 5%, 25%, 50%, 80%, 90%.

Figure 2:
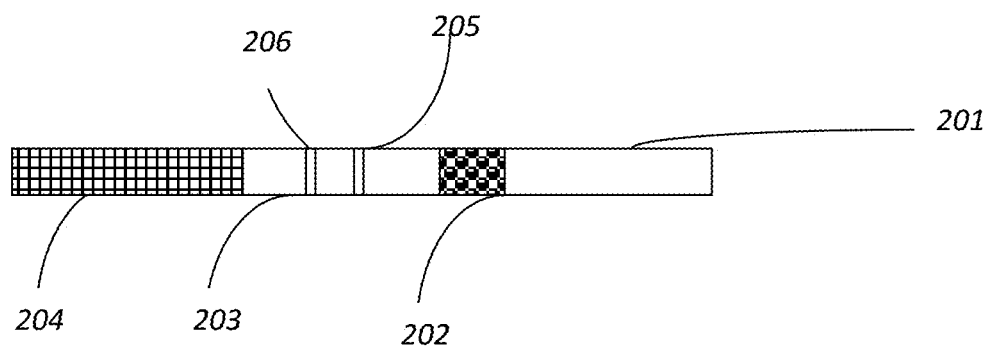
FIG. 2 depicts a structure diagram of a testing element according to another embodiment of the present invention.
Figure 3:
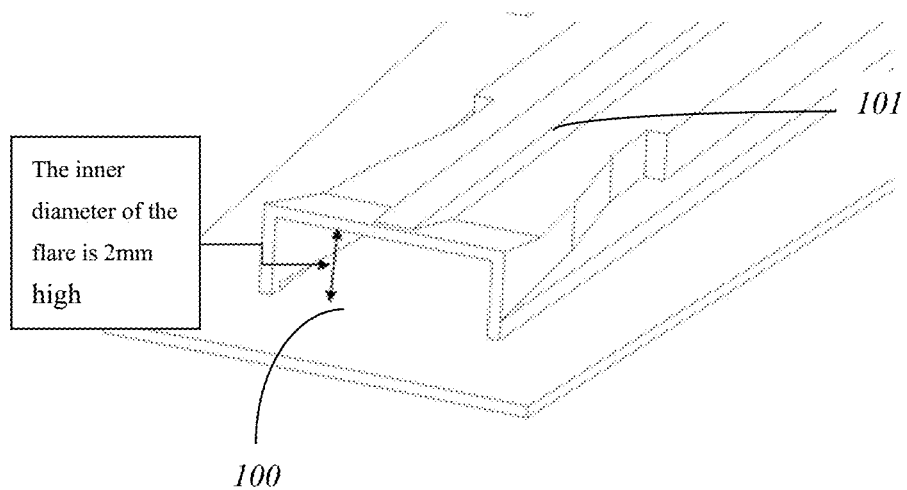
FIG. 3 depicts a structure diagram of a groove of the test card according to an embodiment of the present invention.

For example, as shown in FIGS. 1-3, FIG. 1 is a test card, comprising a plurality of grooves 101 for carrying a carrier, these grooves are injection-molded at one time, the test card has a cover plate 100, and the cover plate adopts a plane structure, for example, a plane plastic sheet is covered on the groove to form a plurality of grooves with an opening end and a closed end, and the test strip is inserted into the groove through the opening end. For example, a test strip as shown in FIG. 2, comprises an absorbing area 201 for absorbing a liquid sample, a marking area 202 for providing a colored marking substance, and a detection area 203 comprising a detection line 205 and a control line 206 of a detection result as well as a water absorbing area 204, and the liquid flows from the absorbing area to the marking area, and then from the marking area, via the detection area 203 and finally to the absorbing area 204, if there is an analyte in the sample, despite of a color appearing or not on the detection line, it is effective when the control line shown color. A colored detection line indicates a positive result, otherwise it indicates a negative result; a darker color indicates a higher content of the analyte. On the contrary, a colored detection line indicates a negative result, otherwise it indicates a positive result; a darker color indicates a lower content of the analyte.

The test area 203 of the inserted test strip faces a plastic plate 100, as the plate is transparent, the presence or absence of a color in the line or a darkness of the colored line on the test area is read by a machine or the naked eyes through the transparent surface, thus to determine an presence of an analyte in the sample.

Figure 4:
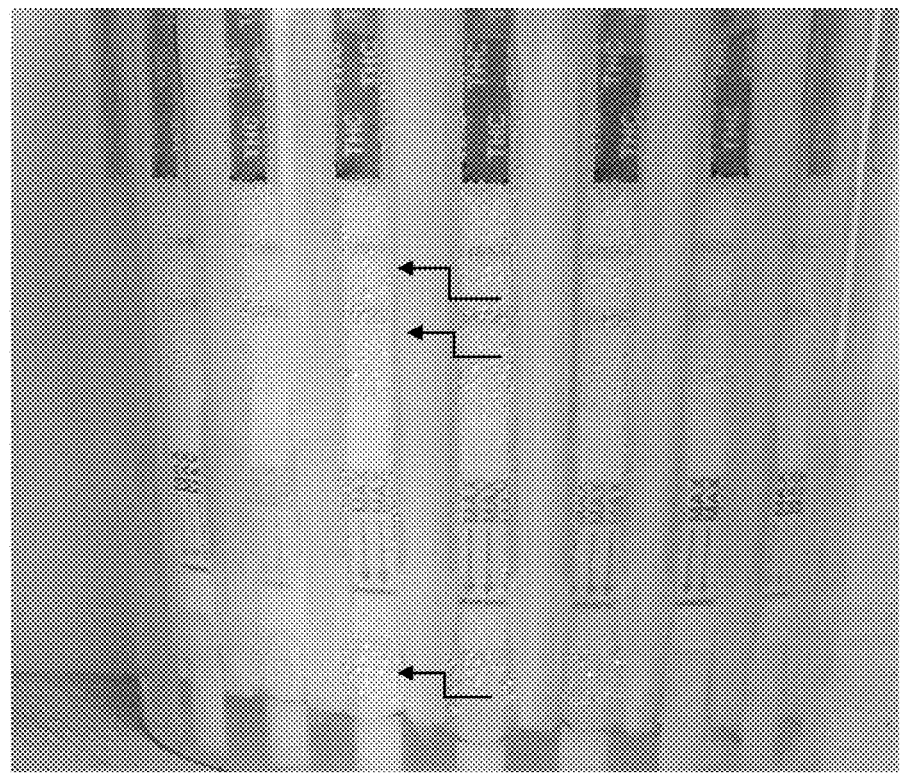
FIG. 4 depicts a test result of a transparent area without anti-mist treatment according to an embodiment of the present invention, wherein the arrow indicates the position where droplets are generated.
Figure 5:
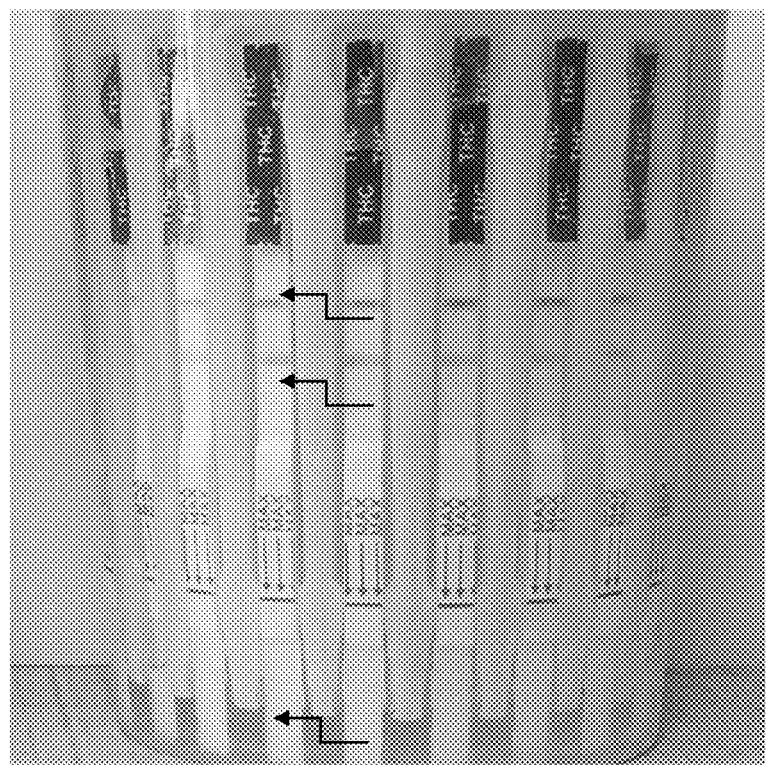
FIG. 5 depicts a test result of a transparent area with anti-mist treatment according to an embodiment of the present invention, wherein the arrow indicates the position where droplets are not generated, and the result is clearly visible.

This test card is generally inserted into a cup body, so that the absorbing area 201 of the test strip contacts a liquid sample in the cup body, such as a urine sample or a fresh urine sample, because the temperature of the urine is generally 35-37° C., while the temperature of the plastic sheet on the test card is at a room temperature of 25° C., or as it is just taken out of a refrigerator, the temperature of the plastic sheet is 15-20° C., at this time, the urine enters into the groove from an entrance to form a micro environment in the groove; the humidity in the groove increases and the moisture content of the air increases, so it is easy to form tiny water droplets on a plane surface, for example the right view shown in FIG. 4 (without any treatment, reference product), there are a plurality of droplets in the transparent sheet of the test area, which cover up the test result of the test area, as indicated by the arrow. However, the plate in the present invention is treated with a layer of anti-mist reagent (with a concentration of 5% xylitol ester), which significantly reduces the generation of droplets, so the result is clearer (FIG. 5).

Figure 6:
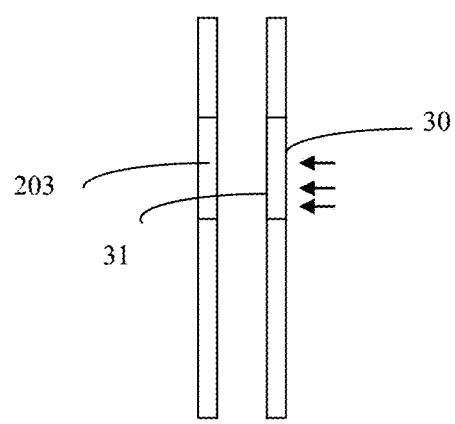
FIG. 6 depicts a structure diagram of a principle demonstration according to the present invention.

For another example, as shown in FIG. 6, the testing element comprises a test area 203 and a transparent area 30 is arranged facing the test area; the transparent area has a surface 31 facing the test area, and the surface is treated or coated with a layer of hydrophilic agent, or the surface is made hydrophobic, even if small droplets (water droplets) are formed on the transparent surface, due to the hydrophilicity the droplets spread into a layer of liquid surface; in this way, the amount of the droplets are reduced, or even if droplets are formed, they may not stay on the surface but flow away directly or fall off due to the action of gravity, thus to avoid mist formation, and further reduces or prevents small droplets from accumulating on the surface of the transparent area.

The content described in the embodiments of the specification is merely an illustration of the implementation embodiments of the present invention, the protection scope of the present invention is not regarded as limited to the specific embodiments described in the embodiments, and the protection scope of the present invention also cover the equivalent techniques in the art Equivalent technical means conceivable by the technicians in the field according to the present invention.

What is claimed is:

1. A detection device, comprising: a testing element, wherein the testing element comprises a detection area configured to detect a presence of an analyte in a liquid sample; and a transparent area through which a test result on the detection area is read, and the transparent area includes a hydrophilic area or a hydrophobic area;
a collecting chamber; and
a blocking element, wherein the testing element is installed in or combined with the collecting chamber, the blocking element fills up the area between the detection area and the inner wall of the transparent area, and the blocking element is configured to reduce or block fluid exchange between the detection area and inner wall of the collecting chamber and surrounding so that a liquid substance originating from the liquid sample cannot enter into the area between the detection area and the inner wall therefore avoiding mist that could affect reading the result on the detection area.

2. The detection device of claim 1, wherein the hydrophilic area or the hydrophobic area faces the detection area.

3. The detection device of claim 1, wherein the hydrophilic area includes a hydrophilic reagent, or the hydrophobic area includes a hydrophobic reagent.

4. The detection device of claim 3, wherein the hydrophilic reagent contains a hydrophilic group.

5. The detection device of claim 3, wherein the hydrophilic reagent contains a surfactant.

6. The detection device of claim 5, wherein the surfactant contains one or several of xylitol ester, sorbitol monopalmitate, lauric acid or stearic acid monoglyceride.

7. The detection device of claim 1, wherein a test area includes an area for displaying a test result.

8. The detection device of claim 7, wherein the test result area is of a line shape.

9. The detection device of claim 1, wherein the detection area substantially and directly contacts the transparent area or the detection area covers on the transparent area.

10. The detection device of claim 9, wherein the detection area covers on the hydrophilic area or the hydrophobic area.

11. The detection device of claim 1, wherein the transparent area is arranged on a carrier, and the carrier comprises the testing element.

12. The detection device of claim 11, wherein the transparent area is arranged on a carrier, and the carrier comprises a groove, and the testing element is arranged in the groove.

13. The detection device of claim 11, wherein the carrier is the collecting chamber for collecting a liquid, the testing element is arranged in the middle of the chamber and the transparent area is arranged on a side wall of the collecting chamber.

14. The detection device of claim 13, wherein the side wall of the chamber adopts a plane structure.

15. The detection device of claim 1, wherein the transparent area is formed by a transparent non-water-absorbent material.

16. The detection device of claim 1, wherein the detection area comprises a porous absorbent material.

17. The detection device of claim 1, wherein the detection area comprises a substance for detecting an analyte.

18. The detection device of claim 16, wherein the porous absorbent material contains any one of nitrocellulose membrane or cellulose acetate membrane or nylon membrane.

19. The detection device of claim 15, wherein the material of the transparent area is any one of transparent glass, plastics, ceramics, plastic thin films, transparent double-sided adhesives, single-sided adhesives, transparent metal films or metal sheets.

20. The detection device of claim 1, wherein the sample is a urine sample.

* * * * *